US009183729B2

(12) United States Patent
Hines et al.

(10) Patent No.: US 9,183,729 B2
(45) Date of Patent: Nov. 10, 2015

(54) HAND CARE REPORTING PANEL

(71) Applicant: DebMed USA LLC, Charlotte, NC (US)

(72) Inventors: John Hines, Cheshire (GB); Dean Philip Limbert, Derby Derbyshire (GB)

(73) Assignee: DEBMED USA LLC, Charlotte, NC (US)

( * ) Notice: Subject to any disclaimer, the term of this patent is extended or adjusted under 35 U.S.C. 154(b) by 101 days.

(21) Appl. No.: 13/801,539

(22) Filed: Mar. 13, 2013

(65) Prior Publication Data

US 2014/0266730 A1    Sep. 18, 2014

(51) Int. Cl.
*G08B 21/00* (2006.01)
*G08B 21/24* (2006.01)
*G06F 19/00* (2011.01)
*A47K 5/12* (2006.01)

(52) U.S. Cl.
CPC ............ *G08B 21/245* (2013.01); *A47K 5/1217* (2013.01); *G06F 19/327* (2013.01)

(58) Field of Classification Search
CPC .................................................. G08B 21/245
USPC ........ 340/573.1, 539.1, 539.13, 521, 3.1, 5.8, 340/13.24; 707/722, 769; 222/1, 52
See application file for complete search history.

(56) References Cited

U.S. PATENT DOCUMENTS

| | | | |
|---|---|---|---|
| 5,945,910 A | 8/1999 | Gorra | |
| 5,954,069 A | 9/1999 | Foster | |
| 6,404,837 B1 | 6/2002 | Thompson | |
| 6,577,240 B2 * | 6/2003 | Armstrong | 340/573.1 |
| 6,707,873 B2 * | 3/2004 | Thompson et al. | 377/13 |
| 6,882,278 B2 | 4/2005 | Winings | |
| 8,558,701 B2 * | 10/2013 | Wegelin et al. | 340/573.1 |
| 2009/0195385 A1 * | 8/2009 | Huang et al. | 340/572.1 |
| 2011/0316701 A1 | 12/2011 | Alper | |
| 2012/0310664 A1 | 12/2012 | Long | |

OTHER PUBLICATIONS

University of Iowa et al., "iScrub Lite 1.5.1", Mar. 25, 2011, XP055147587, Retrieved from Internet: URL:http://compepi.cs.uiowa.edu/iscrub/#handhygiene [retrieved on Oct. 20, 2014].
International Search Report, PCT Application No. PCT/IB2014/001046, Oct. 31, 2014, pp. 1-2.

* cited by examiner

*Primary Examiner* — Toan N Pham
(74) *Attorney, Agent, or Firm* — McAndrews, Held & Malloy, Ltd.

(57) ABSTRACT

A reporting panel reports a selected basis for hand care. The reporting panel may be mounted at a location near one or more hand care product dispensers and may be associated with one or more hand care product dispensers. The reporting panel may communicate with a monitoring system or with a hand care product dispenser.

16 Claims, 5 Drawing Sheets

HAND CARE REPORTING PANEL

RELATED APPLICATIONS

None.

FEDERALLY SPONSORED RESEARCH OR DEVELOPMENT

[Not applicable]

MICROFICHE/COPYRIGHT REFERENCE

[Not applicable]

FIELD

This disclosure relates to identifying and reporting use of hand care products including hand hygiene products and skin care products. Embodiments relate to a reporting panel that is located near a hand care product dispenser and that is operable by a user to report a guideline or circumstance associated with use of the dispenser.

BACKGROUND

Hand care in the workplace implicates both work related activities and worker health. Hand hygiene is essential for certain activities and services including particularly healthcare, food preparation and food service. Hand hygiene is important for virtually all workplaces to maintain a healthy environment and to limit spread of bacteria, viruses and other disease causing micro-organisms. Hand hygiene can be accomplished by washing with soap and water and by using liquids such as a sanitizing product which does not require water or rinsing of the product. Hygiene products that are used for hand hygiene are commonly dispensed by dispensers that are located where hand hygiene is desired. Hand skin care products can promote worker health in avoiding and treating hand skin conditions that can reduce worker performance and productivity. The invention concerns reporting use of hand care product dispensers for both hand hygiene and hand skin care.

The spread of healthcare acquired infections also known as HAI's has been an ever increasing challenge in healthcare facilities. HAIs can result from transmission of bacteria, viruses and other disease causing micro-organisms from various sources such as a patient or environmental surfaces to another patient or surface via the hands of healthcare workers. A consequence of such transmission can be infection of a patient who was previously not infected. Health care facilities have battled MRSA (methicillin-resistant *staphylococcus aureus*) and VRSA (vancomycin-resistant *staphylococcus aureus*) and other drug resistant micro-organisms for many years. These problems have been more apparent in recent years. It is estimated that approximately 2,000,000 such HAIs occur annually in the U.S. alone resulting in about 100,000 deaths. The extra costs associated with these infections are estimated in the billions of dollars.

Healthcare institutions seek to prevent and control the spread of HAIs. One important aspect of such efforts is seeking to ensure that health care professionals comply with hand hygiene best practices. One way to monitor compliance with hand hygiene best practices is to monitor use of hand hygiene product dispensers. Use of such dispensers indicates that hand hygiene has occurred. Dispensers have been adapted to report use such as dispensers disclosed by U.S. patent application Ser. Nos. 12/823,475 and 13/427,467 which are assigned to the applicant of this application and are incorporated herein by reference.

The World Health Organization has identified five moments of hand hygiene in a healthcare setting. Those five moments for hand hygiene actions are shown generally by FIG. 1 at 10. Specifically, the five moments for hand hygiene actions are 1: before patient contact; 2: before performing an aseptic task; 3: after body fluid exposure risk; 4: after patient contact and 5: after contact with patient surroundings. These five moments provide guidelines for hand hygiene within a healthcare setting. Compliance with such guidelines may be evaluated based on monitoring the number of hand hygiene events at locations within a healthcare institution.

Hand hygiene is also recognized as essential in the food industry to prevent the spread of foodborne bacteria and/or viruses including Norovirus, the Hepatitis A virus, *Salmonella Typhi, Shigella* spp., and *Escherichia coli* (*E. coli*) O157:H7 or other Enterohemorrhagic or Shiga toxin-producing *E. coli, Staphylococcus aureus, Salmonella* spp. and *Streptococcus pyogenes*. Hand washing by food employees is essential after activities that contaminate hands and before activities during which pathogens may be spread to food.

The Food and Drug Administration (FDA) recommends that food workers should wash hands when entering a food preparation area; before putting on gloves, including between glove changes; before engaging in food preparation; before handing clean equipment and serving utensils; when changing tasks and switching between handling raw foods and working with ready to eat (RTE) foods; after handling soiled dishes, equipment, or utensils; after touching bare human body parts, for example parts other than clean hands and clean, exposed portions of arms; after using a toilet; after coughing sneezing, blowing his or her nose, using tobacco, eating, or drinking; and after caring for or handling services animals or aquatic animals such as molluscan shellfish or crustaceans in display tanks. Food workers should also wash their hands after any activity that contaminates their hands. These recommendations provide bases for guidelines for hand hygiene in food facilities in which these activities and circumstances occur. Other national food safety agencies similarly recommend good hand hygiene practices, including the Food Standards Agency of the United Kingdom, the European Commission, and Food Standards Australia and New Zealand.

Food safety agencies, including the FDA have developed recommendations for managing facilities based on Hazard Analysis and Critical Control Point (HACCP) systems. Hand hygiene guidelines have been included in systems that are based on HACCP analysis. HACCP is based on seven principles, the fourth of which is monitoring critical control points. Where hand hygiene is essential, HACCP principles call for monitoring of hand hygiene. As for healthcare hand hygiene guidelines, food related hand hygiene guidelines may be evaluated based on monitoring the number of hand hygiene events at a location within a food facility.

Compliance with guidelines or recommended practices for hand care is monitored typically using one of a number of approaches including direct observation, tracking product consumption and more recently electronic monitoring systems have been applied to hand hygiene. Measuring compliance requires knowledge of both the number of hand hygiene events that have occurred (the numerator) and the number of recommended hand hygiene opportunities at which a guideline or recommended practice indicate that hand hygiene should have occurred (the denominator). Direct observation permits both the numerator and denominator to be counted not only at the overall level but also in detail by understanding which recommended hand hygiene opportunities have occurred. Unfortunately direct observation has a number of key deficiencies and problems, notably that it is very expensive to operate, results in only a very small percentage of the total number of hand hygiene opportunities being observed, and carries a well understood risk of over-statement of compliance due to the impact on behavior of being observed (the Hawthorn effect).

Other means of measuring compliance (product consumption, electronic monitoring), typically create a denominator in one of two ways; either the denominator is "measured" based on knowledge of worker location, or the denominator is calculated using statistically validated a-priori observations of hand hygiene opportunities. Examples of these approaches are discussed by U.S. patent application Ser. No. 13/669,988 which is owned by the applicant of this application and is incorporated herein by reference. Location based means of calculating the denominator are difficult and unreliable to align with guidelines such as the WHO 5 moments as the moments do not correlate well with measurable healthcare worker movement patterns, hence statistical based calculations for the denominator are preferred and enable precise calculation not only of the overall number of opportunities but also of the number of opportunities for each of the 5 moments within a statistically valid sample.

In either case however it is currently not possible to align the numerator (the actual number of hand hygiene events that occur) with specific guidelines or recommended practices. Rather the numerator is valid only at the overall level.

BRIEF SUMMARY

An aspect of the present technology provides a reporting panel that communicates with a monitoring system. The reporting panel is operated by a user and reports information about a hand care event for which a hand care product is provided by a dispenser. One application of the present invention is reporting which of a number of guidelines or circumstances is the basis for a hand care event. The present technology may augment a system that monitors dispenser use by identifying a particular guideline or circumstance that is the basis for using the dispenser.

In one aspect of the present technology, a reporting panel has a number of alternatives that may be selected. The alternatives may be presented by individual buttons, regions of a touch panel or other distinct operable or sensing devices that may be associated with guidelines or circumstances to identify a basis for use of a hand care event.

An additional described aspect resides in providing a reporting panel for reporting a guideline or circumstance that is the basis for hand care that may be associated with use of a dispenser within a region of an institution that is proximate to the reporting panel.

An additional described aspect resides in providing a personal reporting panel that may be carried by a worker and that communicates with a monitoring system.

Yet another described aspect resides in providing a personal reporting panel that communicates with a hand care product dispenser that communicates with a monitoring system.

Yet an additional aspect of the present technology relates to a reporting panel that communicates with a dispenser to enable the dispenser to dispense hand care product after the reporting panel is operated to identify the basis for the hand care event.

DESCRIPTION OF EMBODIMENTS

Embodiments described herein concern a reporting panel that communicates directly or indirectly with a monitoring system. The reporting panel reports which of a number of guidelines or circumstances are selected by a user to identify the basis for a hand care event. In particular, embodiments concern a reporting panel that may be associated with one or more hand care product dispensers or with a user of a hand care product dispenser.

Embodiments will be described more fully hereinafter with reference to the accompanying drawings, in which embodiments are shown. Like reference numbers refer to like elements throughout. Other embodiments may, however, be in different forms that are not limited to or by the embodiments set forth herein. Rather, these embodiments are examples. Rights based on this disclosure have the full scope indicated by the claims.

Figure 2:
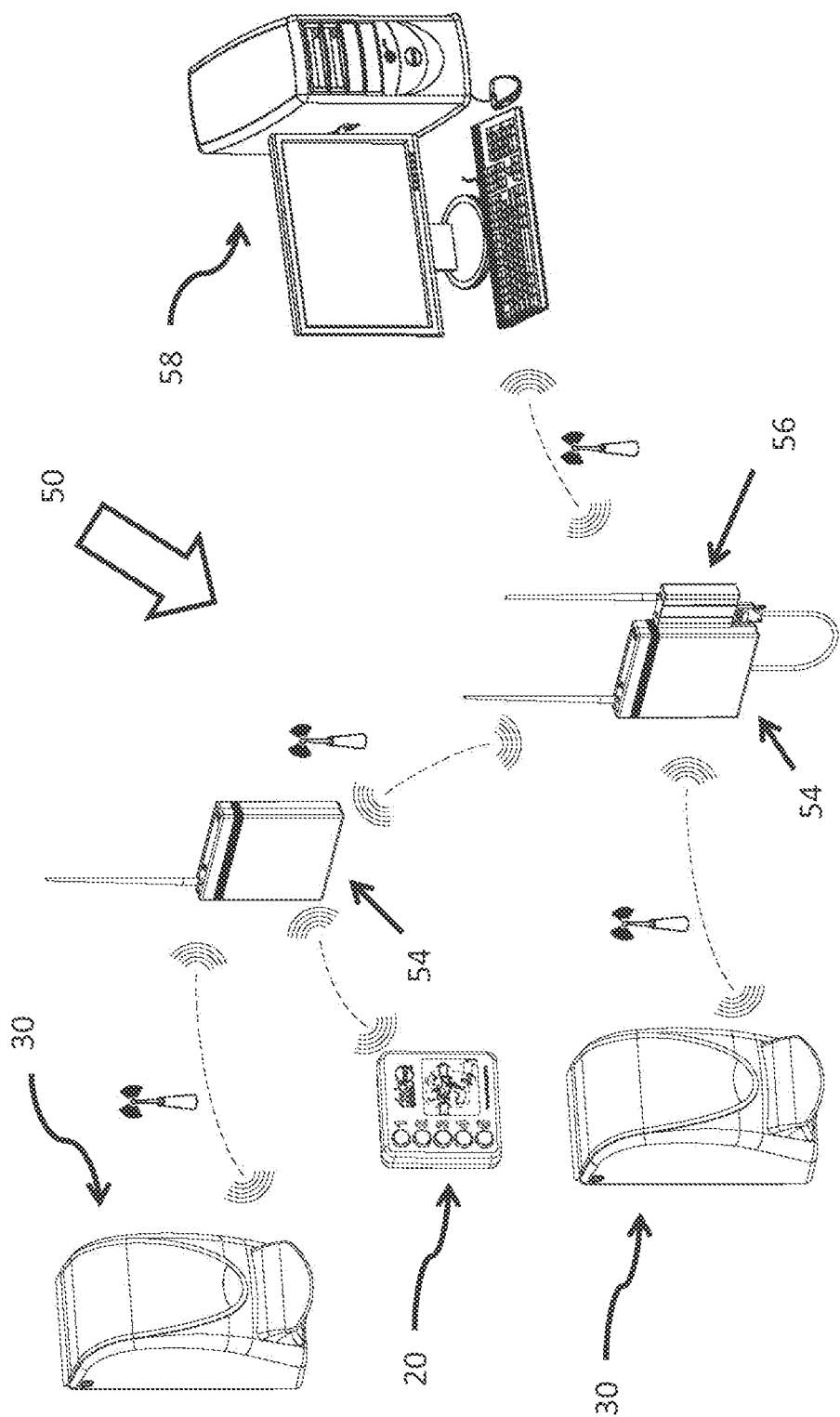
FIG. 2 is a diagram showing a wireless information collection system having hand care product dispensers and a reporting panel.

FIG. 2 is a diagram showing a wireless information collection system that may be used in accordance with the present invention. System 50 is a dispenser usage monitoring system that comprises one or more dispensers 30, a wireless monitoring network, and a data collation server 58. The dispensers 30 communicate with the wireless monitoring network. The depicted wireless system 50 includes two hubs 54 and a gateway 56. The gateway 56 is connected to a data collation server 58. Data may be sent from the gateway 56 to the server 58 in a burst by way of a wired network (e.g., the internet) and/or any cellular network such as GSM. Collected data may also be sent to an offsite server for data processing. U.S. patent application Ser. No. 13/427,467 which is assigned to the owner of this application and is incorporated herein by reference, describes dispensers that include wireless communication, a wireless monitoring network and data collation server. The dispensers 30, wireless network 50 and data collation server 58 of system 50 may operate as described by that application.

The system 50 also includes a reporting panel 20 that is near and associated with one or more dispensers 30. The reporting panel 20 reports which of a number of guidelines or circumstances are selected by a user as a basis for use of an associated dispenser 30. The reporting panel 20 comprises a transmitter that wirelessly reports the selected basis to the wireless monitoring system 50 that, in turn, forwards transmissions to the data collation server 58. The reporting panel 20 connects to the wireless monitoring system in the way that the dispensers 30 connect to the network.

Each reporting panel 20 may be capable of storing data related to up to 100 or more selections. It will be appreciated by those skilled in the art that 100 selections is by way of example only and that typically each reporting panel may need to store data relating to selections of guidelines or circumstances for only a few hand selections. This minimizes the chance of losing data in the event of queuing for receipt by the hub 54. The data is sent between the reporting panel 20 and the hub 54 and between the hub 54 and the gateway 56 in bursts which may be time or memory dependent.

Figure 3:
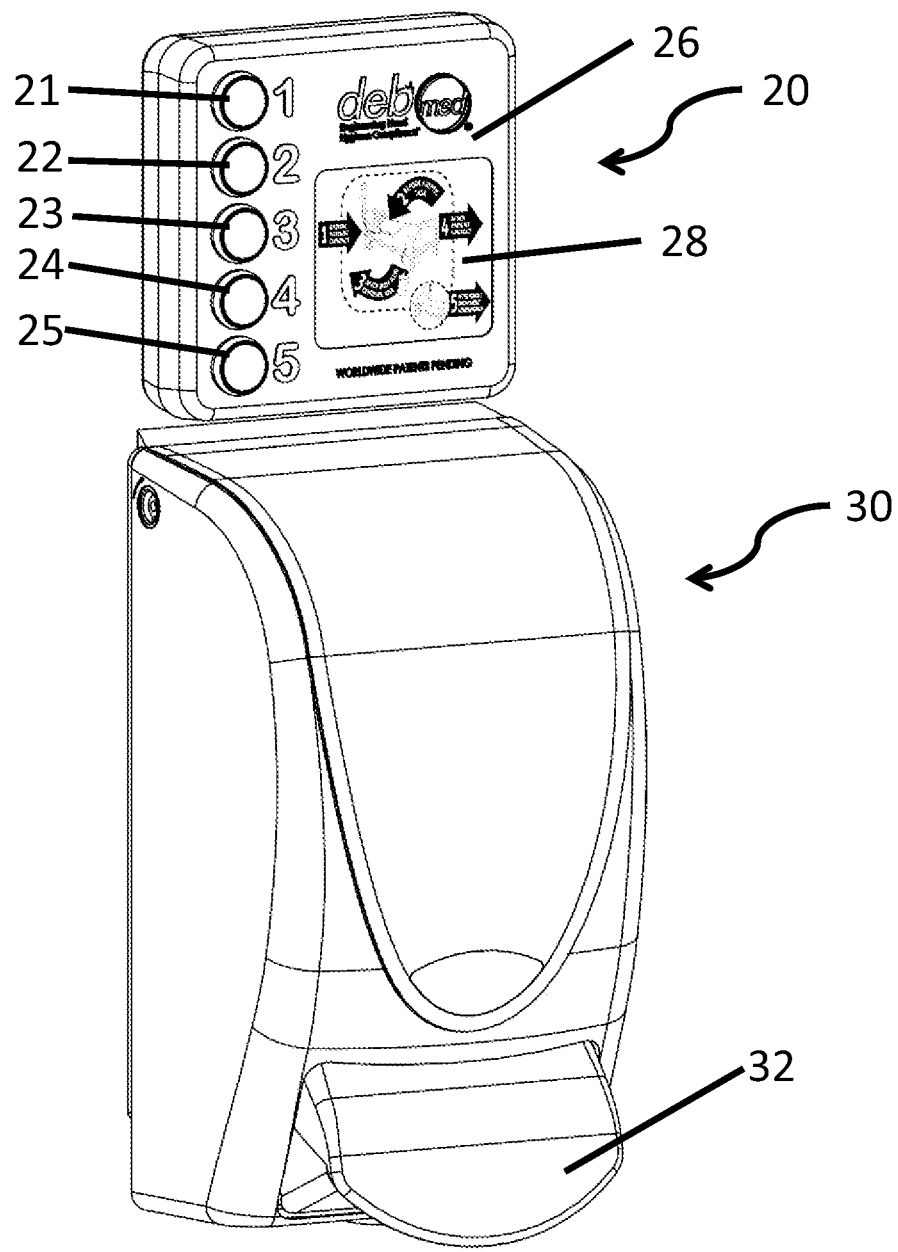
FIG. 3 is an oblique view of a hand care product dispenser and an associated reporting panel.

FIG. 3 illustrates a reporting panel 20 and a hand care product dispenser 30 mounted to a surface S. The hand care product dispenser 30 dispenses a hand hygiene product. The reporting panel 20 is positioned near the dispenser 30. The dispenser 30 includes a lever 32 that is pressed from the front of the dispenser 30 to cause the dispenser 30 to dispense an amount of hand care product. The dispenser 30 includes a wireless transmitter for communication with the monitoring system 50.

Figure 1:
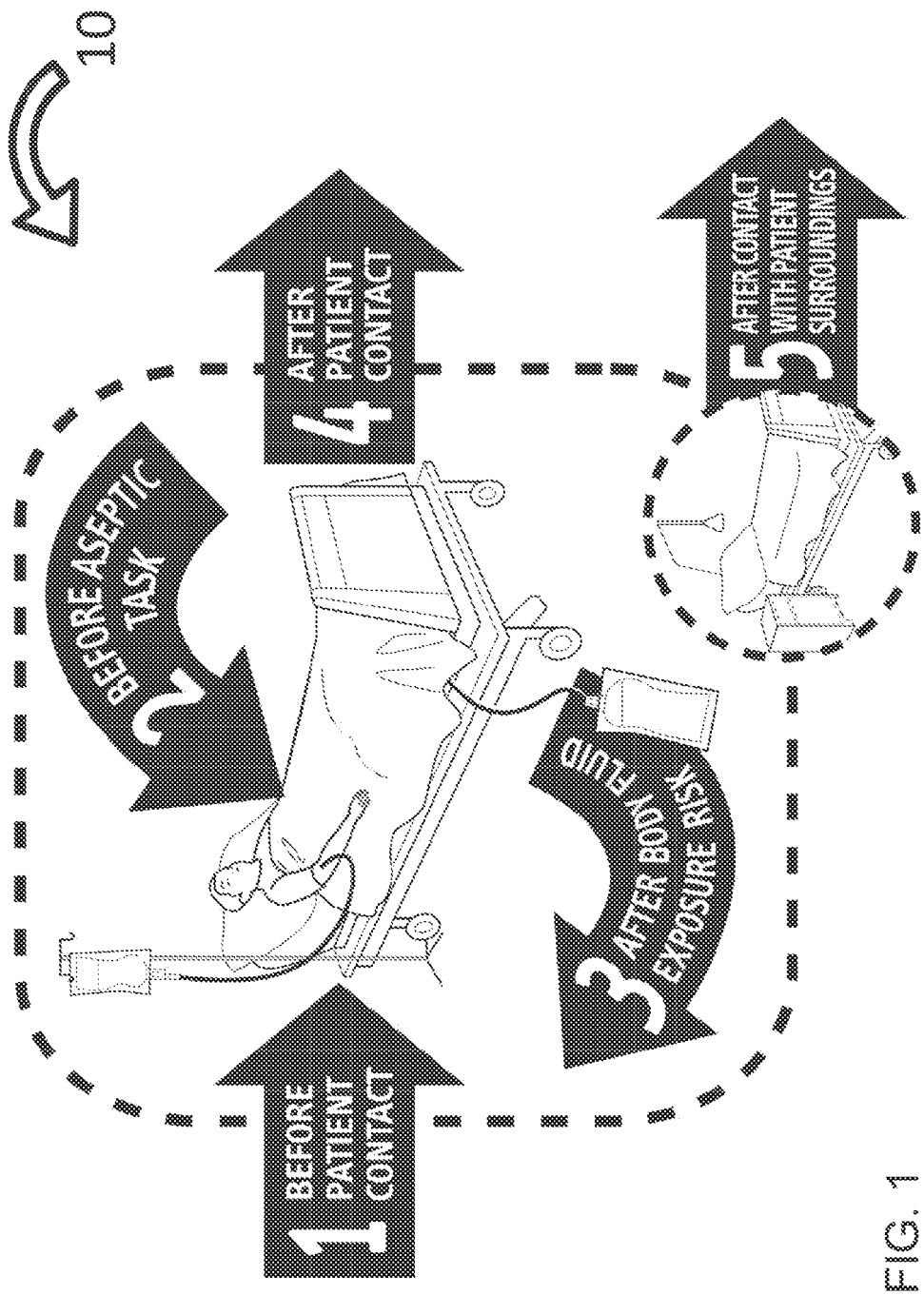
FIG. 1 shows five moments for hand hygiene in a healthcare setting.

The reporting panel 20 includes a surface 26 that faces away from the surface S. Five buttons, 21, 22, 23, 24, and 25 are at the surface 26. The buttons function as sensors that may be individually selected by a user. Adjacent to each button 21, 22, 23, 24, and 25 is a number, 1, 2, 3, 4 and 5, respectively. Each button is thereby labeled as corresponding to one of the five moments of hand hygiene for healthcare that have been identified by the World Health Organization. Also on the surface 26 is a graphic 28 that depicts the World Health Organization recommended five moments of hand hygiene as shown by FIG. 1. A user of the hand care product dispenser 30 can indicate to which of the WHO five moments of hand hygiene a use of the dispenser 30 corresponds by pressing the associated button, 21, 22, 23, 24, or 25 prior to use of the dispenser 30. The reporting panel 20 includes a transmitter, such as that of the dispenser 30, to communicate to the monitoring system 50 which of the buttons has been selected by the user. The reporting panel 20 may also report the time at which the selection was made.

After pressing a button 21, 22, 23, 24, or 25 to select the moment of hand hygiene that is the basis of a hand hygiene event, a user then operates the dispenser 30 to dispense a hand hygiene product for hand hygiene. The dispenser 30 will report that use of the dispenser 30 to the monitoring system 50. The reporting panel 20 is positioned within a convenient distance of the monitor 30, for example within a room in which the dispenser 30 is located. More than one dispenser 30 may be within an area for which a single reporting panel 20 is located. A reported WHO moment selection is associated with a reported subsequent use of a dispenser 30. The moment selection and dispenser use may be associated based on known locations of the reporting panel 20 and dispenser 30 and may also be based on the length of time between reporting panel selection and dispenser use. For example, use of a proximate dispenser within 3 to 4 seconds of a reporting panel selection may be a basis for associating the reporting panel selection with the dispenser use.

Figure 4:
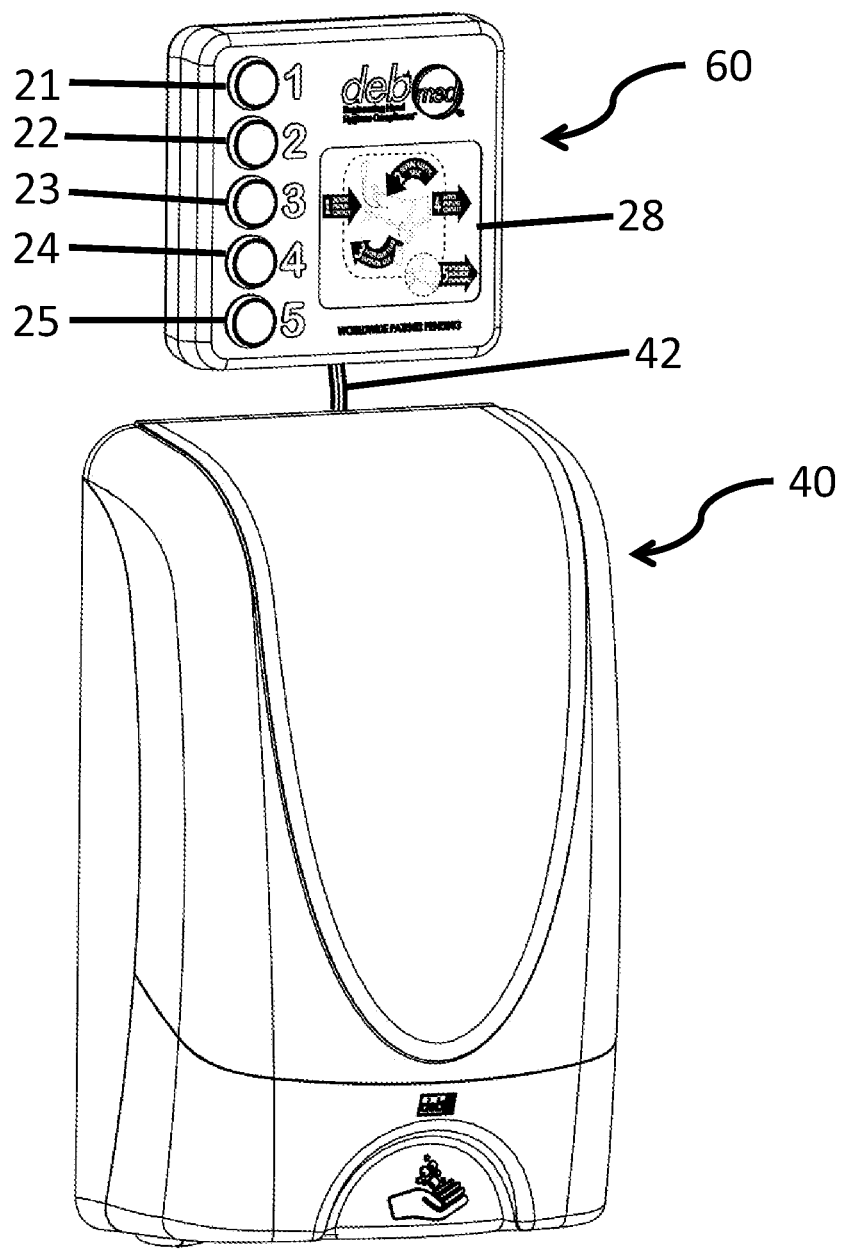
FIG. 4 is an oblique view of a hand care product dispenser with a connected reporting panel.

FIG. 4 illustrates a reporting panel 60 that is positioned adjacent to and communicates with a touch-free dispenser 40. The reporting panel 60 includes the five buttons, 21, 22, 23, 24, and 25 and the graphic 28 that depicts the World Health Organization recommended five moments as described for reporting panel 20. A user identifies a WHO moment by pressing the appropriate button as described for reporting panel 20. Reporting panel 60 does not communicate with a monitoring system as does reporting panel 20. Reporting panel 60 communicates with the dispenser 40 and may do so by a wired connection such as wire 42. The reporting panel 60 reports the selected button to the dispenser 40. The dispenser 40 then reports that selected button to the monitoring system with the report of the dispenser use.

In addition to identifying a selected button to the dispenser 40 for reporting to the monitoring system, the reporting panel 60 may also enable the dispenser 40 to dispense a hand hygiene product. The dispenser 40 is a touch-free dispenser that dispenses a hand hygiene product when a user's hand is sensed to be within a sensor field adjacent to the dispenser 40 where hand hygiene product is dispensed. Dispensing of hand hygiene product by the dispenser 40 may require a prior selection of a button of the reporting panel 60 as a condition of dispensing hand hygiene product. Such a condition may be implemented within hand sensing or automated dispensing electronics of the touch free dispenser 40 so that the dispenser's sensor and drive mechanism are electronically locked until a selection of a button of the reporting panel 60 is recorded.

Figure 5:
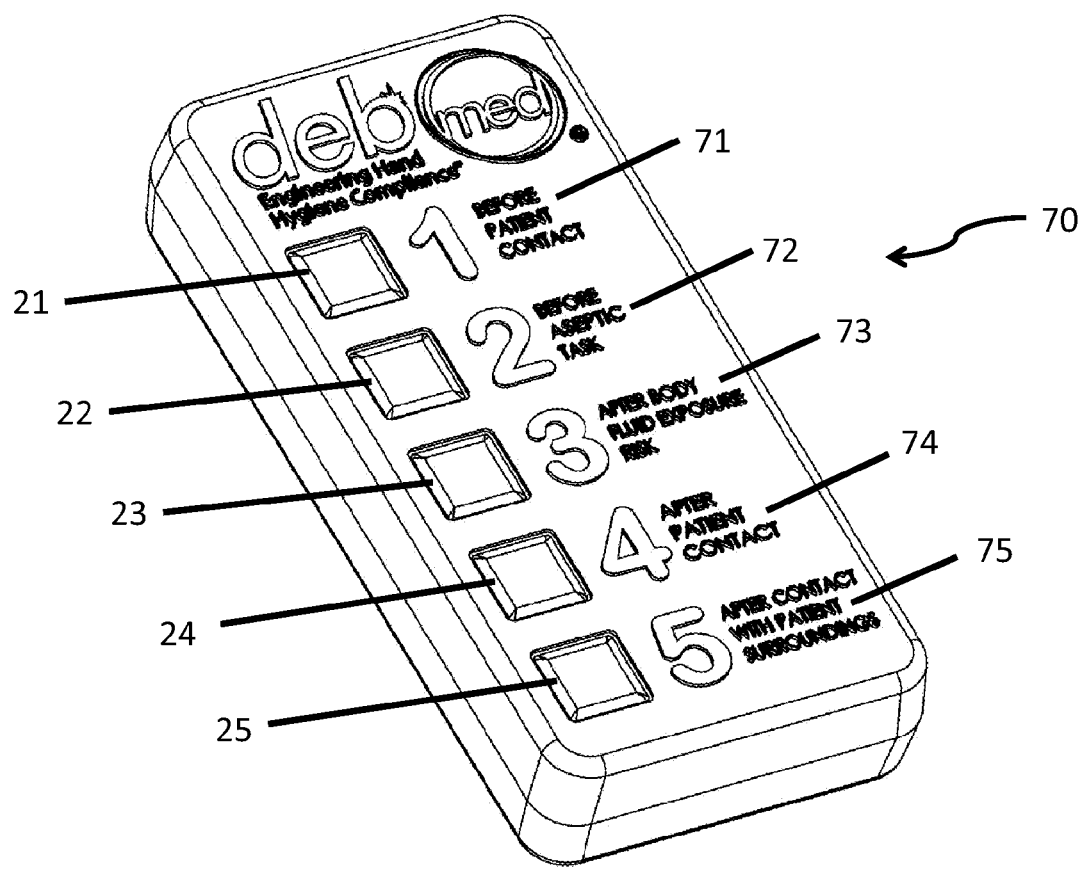
FIG. 5 is an oblique view of a portable reporting panel.

FIG. 5 illustrates a reporting panel 70 that is sized to be carried by a worker and used to report a World Health Organization hand hygiene moment associated with a hand hygiene event. Like reporting panel 20 described above, the reporting panel 70 has five buttons, 21, 22, 23, 24, and 25 that function as sensors that may be individually selected and operated by a user. Adjacent to each button 21, 22, 23, 24, and 25 is a number, 1, 2, 3, 4 and 5, respectively and adjacent to each number is a label, 71, 72, 73, 74 and 75, respectively, that sets out one of the five moments of hand hygiene identified for healthcare by the World Health Organization. The reporting panel 70 reports a WHO moment as the guideline or circumstance for a hand hygiene event.

The reporting panel 70 is not stationary and mounted at a location as is the reporting panel 20. Rather, the reporting panel 70 is carried by a worker. The reporting panel 70 may be carried in a pocket, on a lanyard or clipped to a user's clothing. The reporting panel 70 includes a transmitter that enables the reporting panel 70 to communicate with a monitoring system as described above for the reporting panel 20. As an alternative to communication with the monitoring system, a hand care product dispenser may be configured to receive transmission from the reporting panel 70. A hand care product dispenser that receives an indication of a guideline or circumstance for a hand care event from a reporting panel 70 may report that indication to a monitoring system with the report of the dispenser use as does dispenser 40 as described above. A touch-free hand hygiene product dispenser that receives a transmission from the reporting panel 70 may also require an indication of a basis for a hand care event before dispensing a hand hygiene product, as described above for reporting panel 60 and touch-free hand hygiene product dispenser 40.

The present invention is not limited to embodiments described herein. By way of example, the communication by a dispenser or reporting panel with a monitoring system need not be a wireless communication. Similarly, communication with a data collation server need not be wireless. Communication may be by other means including wired connections and optical communication. A reporting panel may have a selectable sensor other than an operable button, such as a touch screen, a touch-free sensor or other sensor that functions to report different selections by a user. A reporting panel that communicates with a dispenser may be combined with the dispenser to create a single unit rather than two communicating and separated components.

The invention claimed is:
1. A method of monitoring compliance with two or more recommended bases for hand care, the method comprising steps of:
    receiving an indication identifying a recommended basis for hand care;
    receiving an indication that a hand care product dispenser has operated to dispense a hand care product; and
    associating the indication of the basis for hand care with the indicated use of the hand care product dispenser.

2. The method of claim 1, wherein the step of receiving the indication identifying a recommended basis for a hand care receives the indication from a reporting panel with which one of a plurality of recommended bases for hand care may be selected.

3. The method of claim 1, wherein the step of receiving an indication of a basis for hand care and the step of receiving an indication that a hand care product dispenser has operated comprise receiving both indications from the hand care product dispenser.

4. The method of claim 1, wherein the step of receiving an indication of a basis for hand care includes receiving a time that the indication was created, the step of receiving an indication that a hand care product dispenser has operated includes receiving a time that the hand care dispenser operated and the step of the associating the indication of a basis for hand care with the indicated use of the hand care product dispenser comprises determining a length of time between creation of the indication of the basis for hand care and operation of the hand care product dispenser.

5. A method for monitoring bases for use of a hand care product, method comprising the steps of:
 providing a reporting panel with which a basis for use of a hand care product is identified and that communicates an indication of the identified basis and
 providing a monitoring system for receiving an indication of the basis for use of a hand care product from the reporting panel.

6. The method of claim 5, wherein the one of a plurality of recommended bases for use of a hand care product may be selected with the reporting panel.

7. The method of claim 6, wherein the reporting panel is sized and constructed to be carried by a person.

8. The method of claim 5, further comprising the step of providing a hand care product dispenser that communicates an indication that a hand care product has been dispensed and the step of associating the indication of a basis for use of a hand care product with the indication that a hand care product has been dispensed, and wherein the step of providing a monitoring system further comprises providing a monitoring system that receives an indication that a hand care product has been dispensed.

9. The method of claim 8, wherein the step of associating the indication of a basis for use of a hand care product with the indication that a hand care product has been dispensed comprises determining a length of time between identification of the basis for hand care and dispensing of the hand care product.

10. A reporting panel for reporting a basis for use of a hand care product dispenser, the reporting panel comprising:
 a plurality of selectable sensors, at least a subset of the sensors each associated with a basis for hand care;
 a transmitter that communicates an identification of the selected sensor to a monitoring system.

11. The reporting panel of claim 10, wherein the transmitter is a wireless transmitter.

12. The reporting panel of claim 10, wherein the transmitter transmits via a wired connection.

13. A hand care product dispenser comprising:
 a receiver that receives an indication that a basis for hand care has been identified; and
 a dispensing apparatus for dispensing hand care product after the receiver receives indication that a basis for hand care has been identified.

14. The hand care product dispenser of claim 13, wherein the receiver receives wireless communication.

15. The hand care product dispenser of claim 13, further comprising a reporting panel for reporting a basis for use of a hand care product dispenser, the reporting panel including a wireless transmitter and wherein the receiver receives wireless communication from the reporting panel.

16. The hand care product dispenser of claim 13, further comprising a reporting panel for reporting the basis for use of a hand care dispenser, the reporting panel including a wired transmitter, a wired connection connects the reporting panel to the receiver and wherein the receiver receives communication via the wired connection from the reporting panel.

\* \* \* \* \*